United States Patent
Hopper

(10) Patent No.: US 9,635,967 B1
(45) Date of Patent: May 2, 2017

(54) SOCK-DONNING TRIPOD STAND FOR USE WITH AMPUTEE

(71) Applicant: Charles Hopper, Belleview, FL (US)

(72) Inventor: Charles Hopper, Belleview, FL (US)

( * ) Notice: Subject to any disclaimer, the term of this patent is extended or adjusted under 35 U.S.C. 154(b) by 0 days.

(21) Appl. No.: 14/930,863

(22) Filed: Nov. 3, 2015

(51) Int. Cl.
*A47G 25/90* (2006.01)
*A61F 2/78* (2006.01)

(52) U.S. Cl.
CPC .......... *A47G 25/905* (2013.01); *A47G 25/90* (2013.01); *A61F 2/7812* (2013.01); *A61F 2002/7825* (2013.01)

(58) Field of Classification Search
CPC ...... A47G 25/80; A47G 25/90; A47G 25/905; A47G 25/907; A61F 2/78; A61F 2/74; A61F 2/80; A61F 2/7812; A61F 2002/7825
USPC ........................................................ D2/641
See application file for complete search history.

(56) References Cited

U.S. PATENT DOCUMENTS

| | | | |
|---|---|---|---|
| 2,982,453 A * | 5/1961 | Zicarelli | A47G 25/905 223/112 |
| 3,253,812 A * | 5/1966 | Okazaki | B65B 67/12 248/101 |
| 4,488,697 A * | 12/1984 | Garvey | B65F 1/1415 248/101 |
| 6,116,549 A * | 9/2000 | Santa Cruz | B65B 67/12 248/97 |
| D440,740 S | 4/2001 | Anctil | |
| 7,216,787 B2 | 5/2007 | Delamare | |
| D670,883 S * | 11/2012 | Poubouridis | D34/5 |
| 8,656,918 B1 | 2/2014 | Alley | |
| 8,657,165 B1 | 2/2014 | Liu | |
| 2004/0069820 A1 | 4/2004 | Van Loef | |
| 2008/0110945 A1* | 5/2008 | Cookman | A47G 25/905 223/111 |
| 2009/0120975 A1 | 5/2009 | Schoepe | |

FOREIGN PATENT DOCUMENTS

EP 0878157 A1 4/2001
FR WO 2011051582 A2 * 5/2011

\* cited by examiner

*Primary Examiner* — Ismael Izaguirre

(57) ABSTRACT

The sock-donning tripod is adapted for use with stump socks commonly used by amputees. The sock-donning tripod is a free standing structure that is formed with a top plate. The top plate is formed with center cut out and plurality of posts. Each of the plurality of loop of the stump sock are hooked over a post selected from the plurality of posts which holds the stump sock open over the center cut out. The amputation stump can then be placed into the stump sock. The stump sock is then pulled into position using the patient's hand or a dressing stick by using each of the plurality of loops to pull the stump sock into position. The sock-donning tripod comprises a plurality of legs, a top plate, and a brace plate.

6 Claims, 5 Drawing Sheets

SOCK-DONNING TRIPOD STAND FOR USE WITH AMPUTEE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of amputation and caring for amputated limbs, more specifically, a device that assists in the donning of stump socks.

SUMMARY OF INVENTION

The sock-donning tripod is adapted for use with stump socks commonly used by amputees. The sock-donning tripod is a free standing structure that is formed with a top plate. The top plate is formed with center cut out and plurality of posts. Each of the plurality of loop of the stump sock are hooked over a post selected from the plurality of posts which holds the stump sock open over the center cut out. The amputation stump can then be placed into the stump sock. The stump sock is then pulled into position using the patient's hand or a dressing stick by using each of the plurality of loops to pull the stump sock into position.

These together with additional objects, features and advantages of the sock-donning tripod will be readily apparent to those of ordinary skill in the art upon reading the following detailed description of the presently preferred, but nonetheless illustrative, embodiments when taken in conjunction with the accompanying drawings.

In this respect, before explaining the current embodiments of the sock-donning tripod in detail, it is to be understood that the sock-donning tripod is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the sock-donning tripod.

It is therefore important that the claims be regarded as including such equivalent construction insofar as they do not depart from the spirit and scope of the sock-donning tripod. It is also to be understood that the phraseology and terminology employed herein are for purposes of description and should not be regarding as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
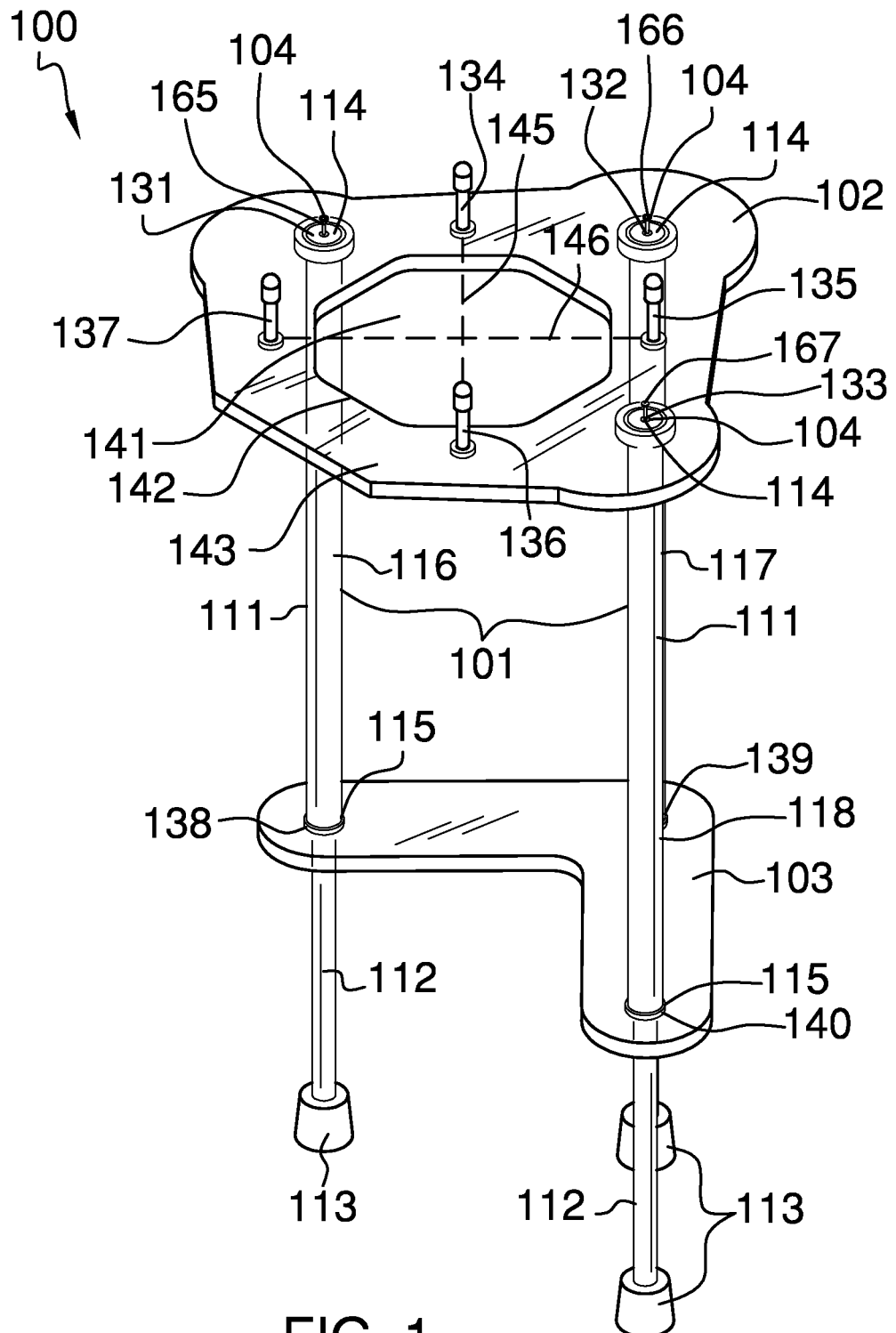
FIG. 1 is a perspective view of an embodiment of the disclosure.
Figure 2:
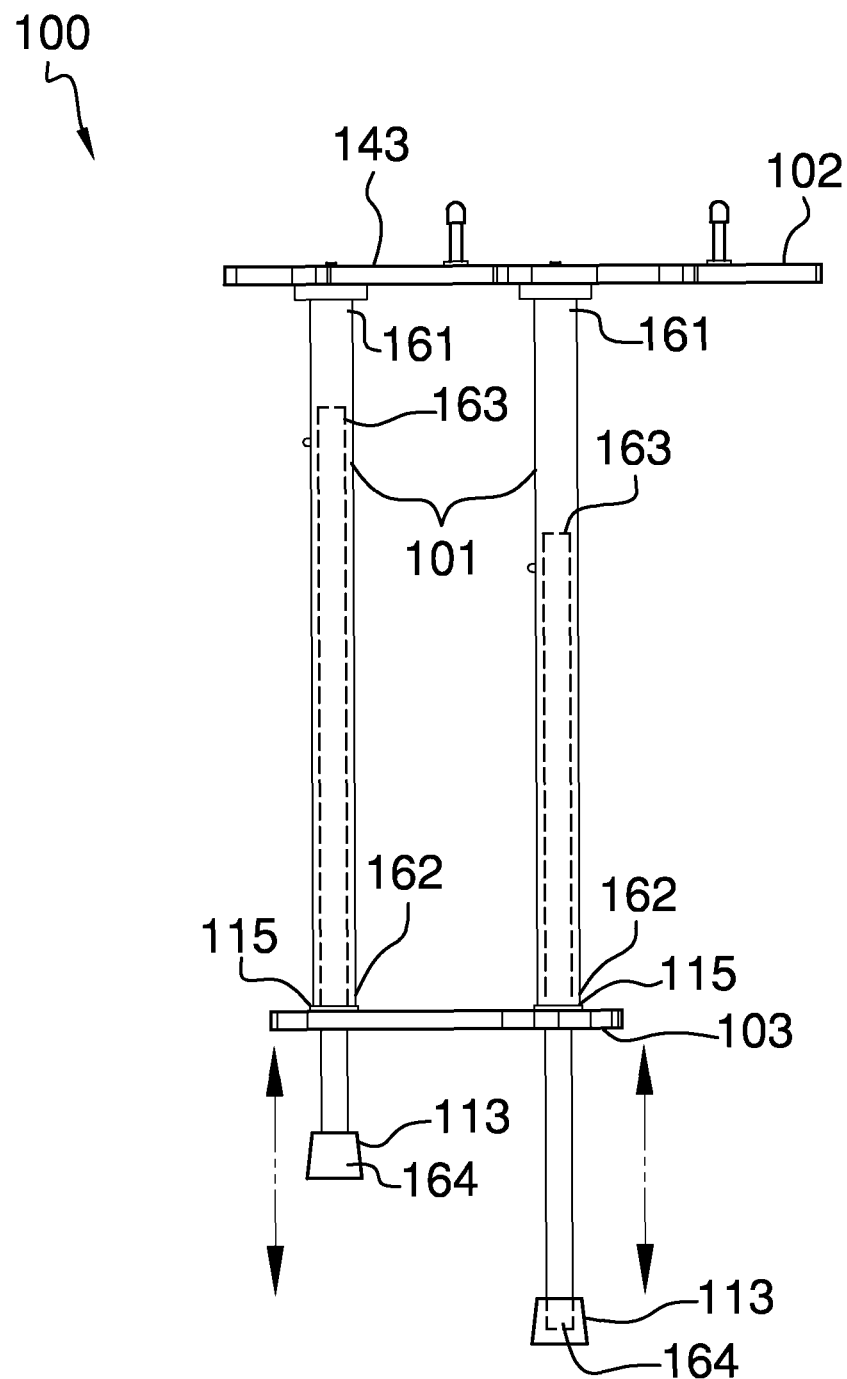
FIG. 2 is a side view of an embodiment of the disclosure.
Figure 3:
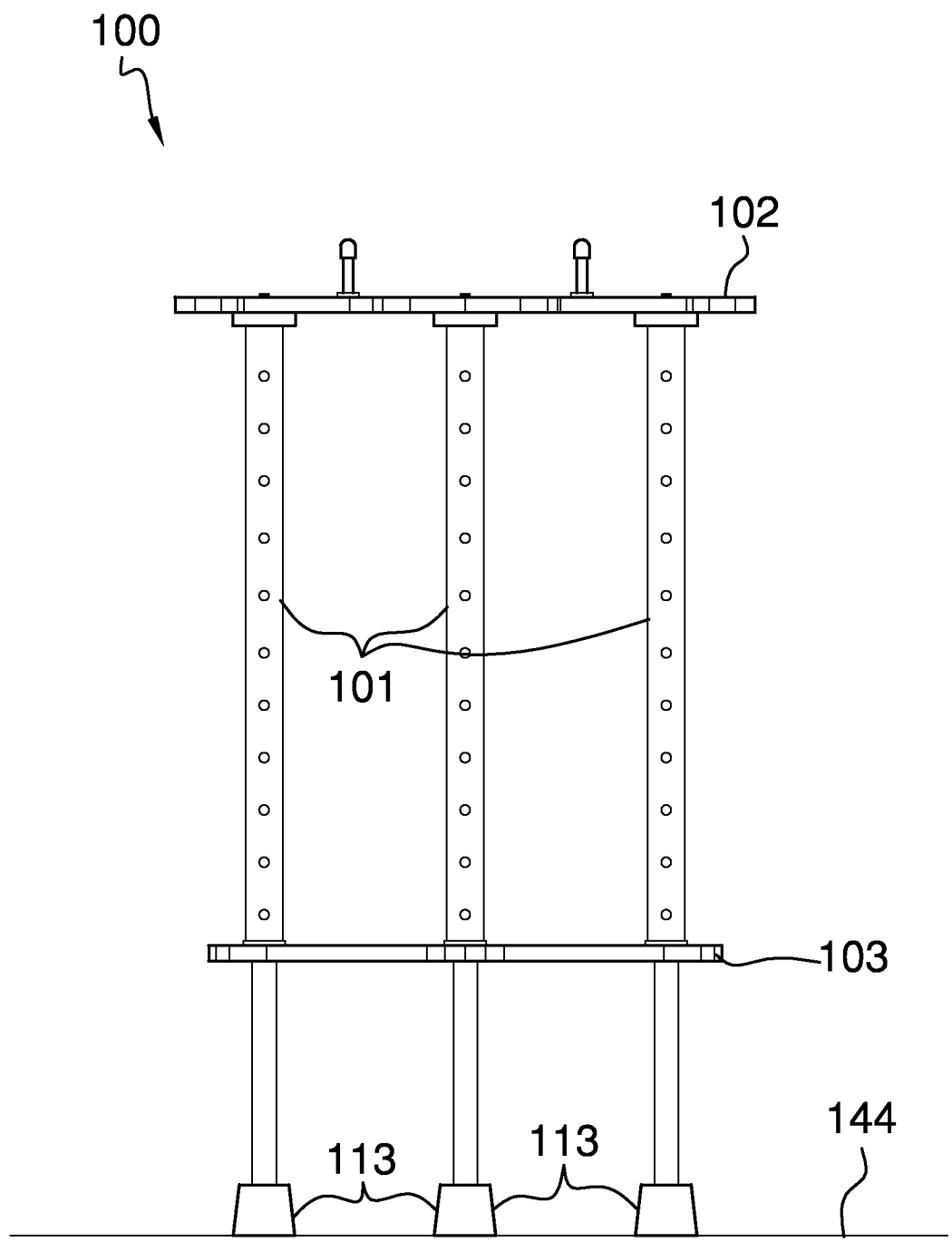
FIG. 3 is a back view of an embodiment of the disclosure.
Figure 4:
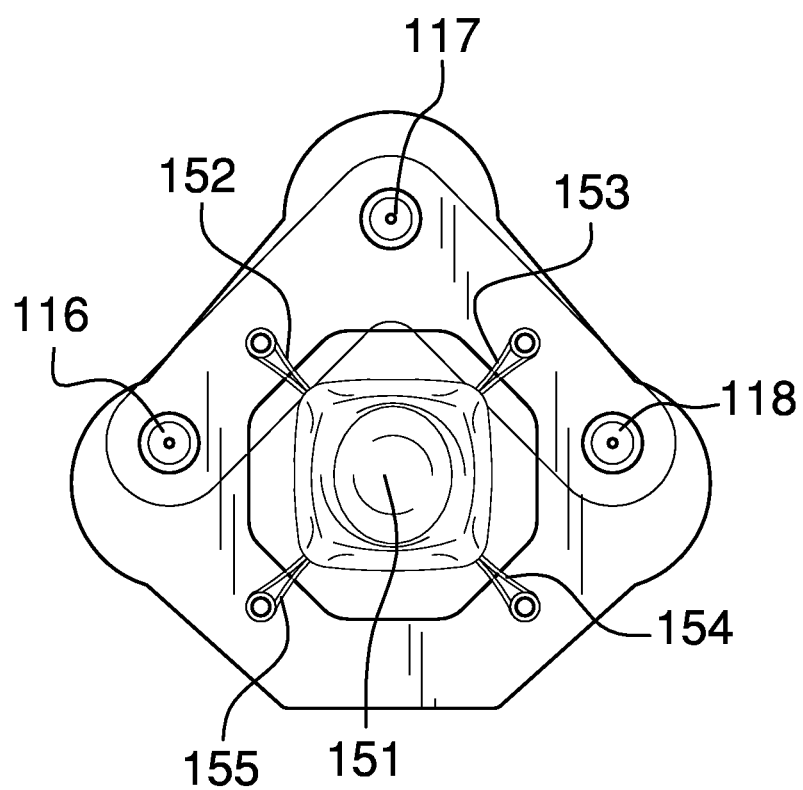
FIG. 4 is a top view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 5. The sock-donning tripod 100 (hereinafter invention) comprises a plurality of legs 101, a top plate 102, and a brace plate 103.

Each of the plurality of legs 101 further comprises an upper segment 111, a lower segment 112, a cane tip 113, a threaded hole 114, and a locking mechanism 115. The upper segment 111 is a capped pipe. The upper segment 111 is further defined with a first end 161 and a second end 162. The first end 161 is the capped end of the upper segment 111 and the second end 162 is the open end of the upper segment 111. The lower segment 112 is a pipe. The lower segment 112 is further defined with a third end 163 and a fourth end 164. The outer diameter of the lower segment 112 is sized to fit within the inner diameter of the upper segment 111. Each of the plurality of legs 101 is assembled in a telescopic arrangement wherein the third end 163 of the lower segment 112 is inserted into the second end 162 of the upper segment 111. The lower segment 112 and the upper segment 111 are joined by the locking mechanism 115. The locking mechanism 115 is a commercially available device that is used to attach the lower segment 111 to the upper segment 111 and to hold the lower segment 112 in a constant position relative to the upper segment 111. Adjustable locking devices for telescopic assemblies are well known and documented in the art. The first end 161 of the upper segment 111 has formed in it a threaded hole 114. The threaded hole 114 is discussed elsewhere in this disclosure. The fourth end 164 of the lower segment 111 is capped with a cane tip 113. The cane tip 113 is a readily and commercially available protective device that protects floors from damage by the lower segment 112 and prevents the invention 100 from slipping during use.

The plurality of legs 101 further comprises a first leg 116, a second leg 117, and a third leg 118. The top plate 102 is a plastic structure that is mounted to the first end 161 of the first leg 116, the first end 161 of the second leg 117 and the first end 161 of the third leg 118. Positioned within the perimeter of the top plate 102 is a center cut out 141. The center cut out 141 is a hole that is formed in the shape of a regular octagon 142. The center of the regular octagon 142 is positioned such that: 1) when the fourth end 164 of the first leg 116, the fourth end 164 of the second leg 117 and the fourth end 164 of the third leg 118 are placed on a level resting surface 144; such that, 2) the top surface 143 of the top plate 102 is parallel to the level resting surface 144; then, 3) a line drawn from the center of the regular octagon 142 through the center of mass of the invention 100 will perpendicularly intersect the level resting surface 144. The top plate 102 further comprises a first hole 131, a second hole 132, and a third hole 133. The first hole 131 is positioned such that the center of the first hole 131 is aligned with the threaded hole 114 of the first leg 116. The second hole 132 is positioned such that the center of the second hole 132 is aligned with the threaded hole 114 of the second leg 117. The third hole 133 is positioned such that the center of the third hole 133 is aligned with the threaded hole 114 of the third leg 118.

The top plate 102 is attached to the first leg 116, the second leg 117, and the third leg 118 using a plurality of bolts 104. Each bolt selected from the plurality of bolts 104 is sized to fit through either the first hole 131, the second hole 132 or the third hole 133. Each of the plurality of bolts 104 is threaded such that each of the plurality of bolts 104 will fit into either the threaded hole 114 of the first leg 116, the threaded hole 114 of the second leg 117, or the threaded hole 114 of the third leg 118. The plurality of bolts 104 further comprises a first bolt 165, a second bolt 166 and a third bolt 167. To attach the top plate 102 to the plurality of legs 101, the first hole 131 is placed over the threaded hole 114 of the first leg 116 and is secured using the first bolt 165. The second hole 132 is placed over the threaded hole 114 of the second leg 117 and is secured using the second bolt 166. The third hole 133 is placed over the threaded hole 114 of the third leg 118 and is secured using the third bolt 167.

The top plate 102 further comprises a first post 134, a second post 135, a third post 136, and a fourth post 137. The first post 134 is a metal post that projects perpendicularly away from the top surface 143 in a direction away from the resting surface 144. The second post 135 is a metal post that projects perpendicularly away from the top surface 143 in a direction away from the resting surface 144. The third post 136 is a metal post that projects perpendicularly away from the top surface 143 in a direction away from the resting surface 144. The fourth post 137 is a metal post that projects perpendicularly away from the top surface 143 in a direction away from the resting surface 144. The first post 134 and the third post 136 are positioned such that a first line drawn 145 from the first post 134 and the third post 136 will intersect a second line drawn 146 between the second post 135 and the fourth post 137 at a right angle 147.

The first leg 116, the second leg 117 and the third leg 118 are braced using the brace plate 103 to prevent lateral movement. The brace plate 103 is a rigid "L" shaped structure. The brace plate 103 further comprises a fourth hole 138, a fifth hole 139 and a sixth hole 140. The fourth hole 138 is sized to receive the upper segment 111 of the first leg 116. The fifth hole 139 is sized to receive the upper segment 111 of the second leg 117. The sixth hole 140 is sized to receive the upper segment 111 of the third leg 118. The first leg 116 is inserted and secured through the fourth hole 138. The second leg 117 is inserted and secured through the fifth hole 139. The third leg 118 is inserted and secured through the sixth hole 140.

Figure 5:
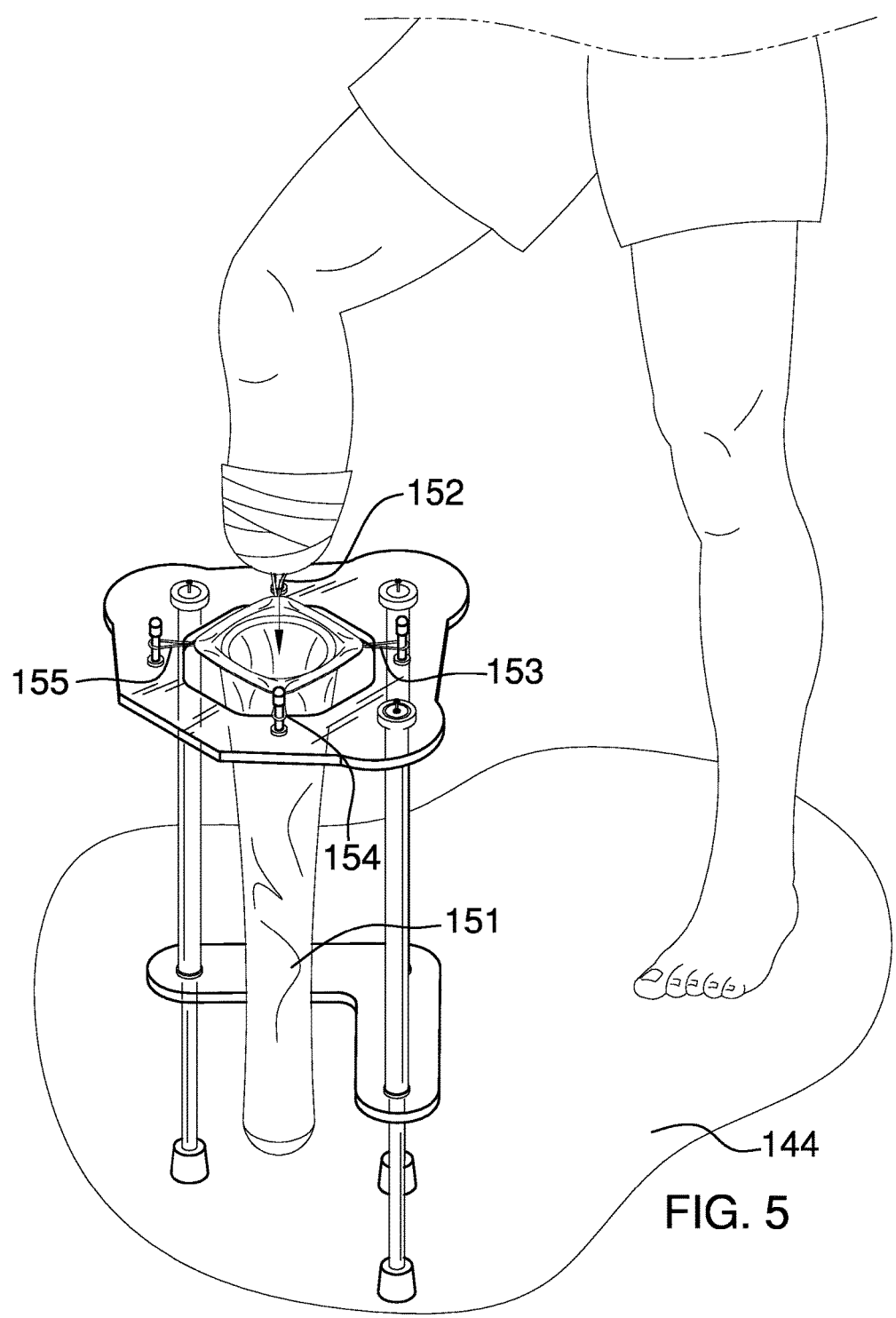
FIG. 5 is an in use view of an embodiment of the disclosure.

To use the invention 100, the invention 100 is placed on a resting surface 144 by adjusting the length of the first leg 116, the length of the second leg 117 and the length of the third leg 118 such that the top plate 102 is positioned in a location that is comfortable user. The stump sock 151 is placed through the center cut out 141. As shown in FIG. 5, the first loop 152 of the stump sock 151 is secured over the first post 134, the second loop 153 of the stump sock 151 is secured over the second post 135, the third loop 154 of the stump sock 151 is secured over the third post 136, the fourth loop 155 of the stump sock 151 is secured over the fourth post 137. The using their hand or a dressing stick the user than pulls up the first loop 152 of the stump sock 151, the second loop 153 of the stump sock 151, the third loop 154 of the stump sock 151, and the fourth loop 155 until the stump sock 151 to a comfortable position.

Each of the plurality of legs 101 is made from aluminum. The top plate 102 and the brace plate 103 are formed from plastic. Suitable plastics include, but are not limited to, polycarbonate or poly(methyl methacrylic). The first post 134, second post 135, third post 136 and fourth post 137 are formed from aluminum. The locking mechanism 115 is commercially available.

The following definitions were used in this disclosure:

Capped Pipe: As used in this disclosure, a capped pipe is a pipe with one closed end and one open end.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; or, 4) the point, pivot, or axis around which something revolves.

Inner Diameter: As used in this disclosure, the term inner diameter is used in the same way that a plumber would refer to the inner diameter of a pipe.

Outer Diameter: As used in this disclosure, the term outer diameter is used in the same way that a plumber would refer to the outer diameter of a pipe.

Perimeter: As used in this disclosure, a perimeter is one or more curved or straight lines that bounds an enclosed area on a plane.

Pipe: As used in this disclosure, a pipe is a hollow cylindrical device that is used for transporting liquids and gasses. The line that connects the center of the first base of the cylinder to the center of the second base of the cylinder is referred to as the axis of the cylinder or the centerline of the pipe. When two pipes share the same centerline they are said to be aligned.

Telescopic: As used in this disclosure, telescopic is an adjective that describes an object made of sections that fit or slide into each other such that the object can be made longer or shorter by adjusting the relative positions of the sections.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A sock-donning tripod comprising:
a plurality of legs, a top plate, and a brace plate;
wherein the sock-donning tripod is adapted for use by a person with a leg amputations;
wherein the sock-donning tripod is adapted for use with stump socks;
wherein the sock-donning tripod is adapted for use on a resting surface;
wherein the sock-donning tripod holds the stump sock in a fixed position to allow the person with a leg amputation to don the stump sock;
wherein each of the plurality of legs further comprises an upper segment, a lower segment, a cane tip, a threaded hole, and a locking mechanism;
wherein the upper segment is a capped pipe;
wherein the upper segment is further defined by a first end and a second end;
wherein the lower segment is a pipe;
wherein the lower segment is further defined with a third end and a fourth end;
wherein the outer diameter of the lower segment is less than the inner diameter of the upper segment;
wherein each of the plurality of legs is assembled in a telescopic arrangement;
wherein the lower segment and the upper segment are joined by the locking mechanism;
wherein the locking mechanism holds the lower segment in a constant position relative to the upper segment;
wherein the plurality of legs further comprises a first leg, a second leg, and a third leg;
wherein the top plate is a plastic structure that is attached to the first leg, the second leg and the third leg;
wherein the top plate is further defined with a top surface;
wherein a center cut out is formed within the perimeter of the top plate;
wherein the center cut out is a hole that is formed in the shape of a regular octagon;
wherein the top plate further comprises a first post, a second post, a third post, and a fourth post.

2. The sock-donning tripod according to claim 1 wherein the first post is a metal post that projects perpendicularly away from the top surface;
wherein the second post is a metal post that projects perpendicularly away from the top surface;
wherein the third post is a metal post that projects perpendicularly away from the top surface;
wherein the fourth post is a metal post that projects perpendicularly away from the top surface.

3. The sock-donning tripod according to claim 2 wherein the first post, the second post, the third post, and the fourth post are positioned on the top plate such that a first line drawn from the first post and the third post will intersect a second line drawn between the second post and the fourth post at a right angle.

4. The sock-donning tripod according to claim 3 wherein the brace plate is a rigid "L" shaped structure.

5. The sock-donning tripod according to claim 4 wherein the brace plate further comprises a first hole, a second hole and a third hole.

6. The sock-donning tripod according to claim 5 wherein the first hole is sized to receive the first leg;
wherein the second hole is sized to receive the second leg;
wherein the third hole is sized to receive the third leg.

* * * * *